(12) United States Patent
Hwang (10) Patent No.: US 6,766,695 B2
(45) Date of Patent: Jul. 27, 2004

(54) HALT/HASS FIXTURING TABLE FOR GENERATING SECONDARY VIBRATION USING MOVING BALLS AND MULTI-AXES RAILS

(76) Inventor: Chung Shick Hwang, 67-330, Jeggi2-dong, Dongdaemun-gu, Seoul city, 130-062 (KR)

(*) Notice: Subject to any disclaimer, the term of this patent is extended or adjusted under 35 U.S.C. 154(b) by 0 days.

(21) Appl. No.: 10/279,173

(22) Filed: Oct. 24, 2002

(65) Prior Publication Data

US 2003/0089175 A1 May 15, 2003

(30) Foreign Application Priority Data

Nov. 12, 2001 (KR) ................................ 20-2001-0034626

(51) Int. Cl.$^7$ .............................................. B06B 3/00
(52) U.S. Cl. ...................................................... 73/663
(58) Field of Search ...................... 73/662–664, 866.5, 73/865.9

(56) References Cited

U.S. PATENT DOCUMENTS

| | | | | | |
|---|---|---|---|---|---|
| 5,083,463 A | * | 1/1992 | Marshall et al. | ............... | 73/663 |
| 5,594,177 A | * | 1/1997 | Hanse | ..................... | 73/663 |
| 5,804,732 A | * | 9/1998 | Wetzel et al. | ................. | 73/663 |
| 5,969,256 A | * | 10/1999 | Hobbs | ......................... | 73/663 |
| 6,105,433 A | * | 8/2000 | Hess | ............................ | 73/663 |
| 6,220,100 B1 | * | 4/2001 | Felkins et al. | ................ | 73/663 |

* cited by examiner

Primary Examiner—Helen Kwok
(74) Attorney, Agent, or Firm—Porter, Wright, Morris & Arthur, LLP (57) ABSTRACT

The present invention provides a HALT/HASS fixturing table for generating secondary vibration using moving balls and multi-axes rails comprising a lower panel having on the top surface thereof a plurality of horizontal rails and vertical rails formed in the shape of grooves, moving balls inserted in the horizontal rails and the vertical rails of the lower panel to move in the horizontal and the vertical rails, a buffering member placed on the lower panel, and a upper panel placed on the buffering member, a specimen for the HALT/HASS test being attached to the upper panel.

4 Claims, 7 Drawing Sheets

HALT/HASS FIXTURING TABLE FOR GENERATING SECONDARY VIBRATION USING MOVING BALLS AND MULTI-AXES RAILS

FIELD OF THE INVENTION

The present invention relates to a HALT/HASS fixturing table for generating secondary vibration using moving balls and multi-axes rails. More particularly, the present invention relates to a HALT/HASS fixturing table mounted on a device for generating primary vibration to generate multi-axes complex waves in 6 degrees of freedom, so that HALT/HASS test (HALT: High Accelerated Life test & HASS: High Accelerated Stress Screening) can be conducted more efficiently and can be conducted with conventional devices for generating vibration.

BACKGROUND OF THE INVENTION

Generally, prior to mass production of goods provided to consumers, a reliability test is conducted to check the quality and performance of the goods in order to reduce inferior goods and to assure the high quality and reliability of the products.

The reliability test is divided into a climatic reliability test and a mechanical reliability test. The climatic reliability test is to check the influence of environmental conditions such as temperatures, humidity and atmosphere on products, and the mechanical reliability test is to check the influence of conditions such as vibration, shock, impact and collision on products.

Recently, such environmental conditions have become more severe, accelerated and varied to improve failure margin and improve incompleteness of products. The HALT/HASS test is one of the recently developed mechanical reliability tests which have been put to practical use in advanced countries.

In the meantime, vibrational reliability test commonly conducted comprises the steps of: placing a test product on a vibration generator; generating vibration of a certain frequency (e.g., shortened frequency of sine wave, shortened frequency range of random wave and shock wave) by the vibration generator; and observing vibration characteristics of the test product in the certain frequency to check on which point of vibration, i.e., on which resonance point the test product is destroyed.

As mentioned above, conventional vibrational reliability test is to measure the vibration point on which a test product is destroyed by generating a certain frequency of unidirectional wave such as sine wave, shortened frequency range of random wave or shock wave. On the other hand, the HALT/HASS test is to measure the reliability of a test product by using wide frequency range of repetitive shock vibration and simultaneous multi-axes complex waves of 6 degrees of freedom in order to measure failure margin of the product.

Figure 8:
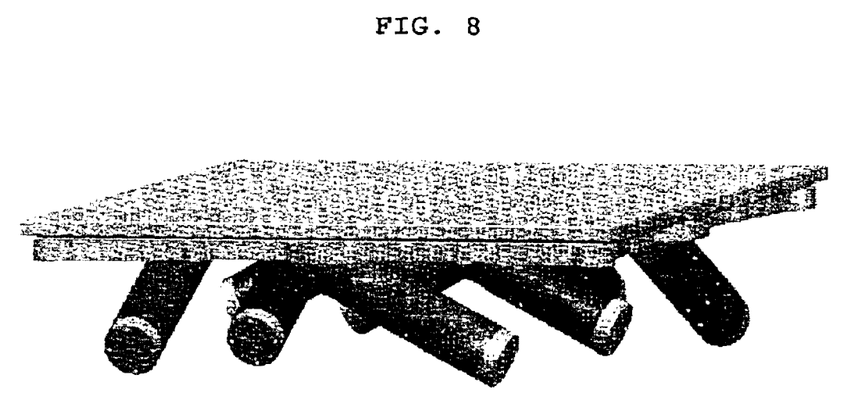
FIG. 8 shows a vibration table for the HALT/HASS test using conventional pneumatic cylinders.

However, a repetitive shock vibration table in 6 degrees of freedom which has been used in the conventional HALT/HASS test method used a pneumatic vibration mechanism which is composed of pneumatic cylinders and a rigid aluminum or magnesium table (see FIG. 8). In case of using this conventional pneumatic vibration mechanism, since the vibration spectrum was fixed by the pneumatic vibration cylinders and the structural design of the table, it was not easy for the conventional HALT/HASS test to adapt itself to various test specimens. Also, since an effect of causing acceleration deteriorates due to the fixed vibration spectrum and the lowered maximum vibration level in the low frequency zone, the conventional HALT/HASS test was not effective.

Effective frequency zone in the HALT/HASS test depends on the mass of a test specimen and structural conditions of the fixed vibration spectrum of pneumatic vibration mechanism.

That is, as vibration spectrum in relatively low frequency zone is effective for massive and complex test specimen, and vibration spectrum in high frequency zone is effective for lightweight and simple test specimen, the HALT/HASS test with the fixed vibration spectrum of pneumatic vibration mechanism has difficulties in conducting an effective test for the variety of test specimens.

Figure 9:
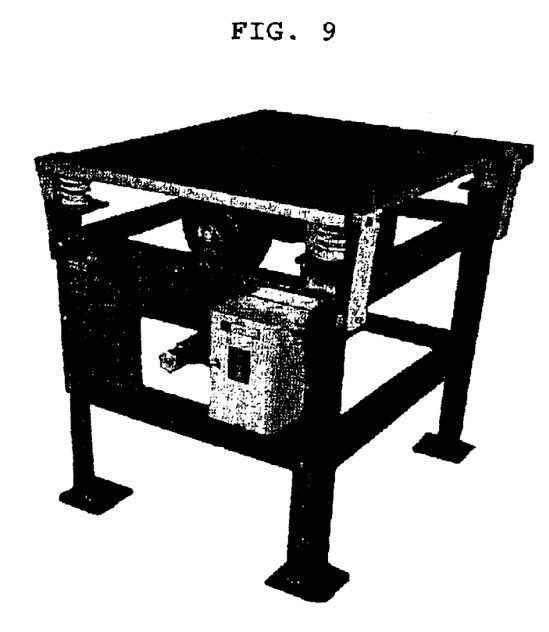
FIG. 9 shows a device for generating mechanical vibration.
Figure 10:
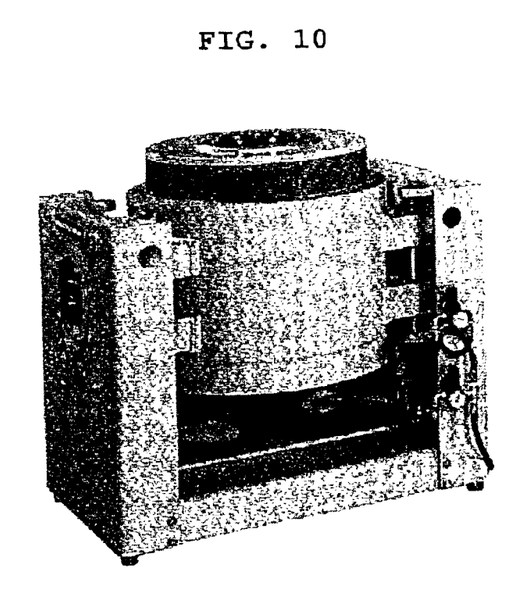
FIG. 10 shows a device for generating electromagnetic vibration.
Figure 11:
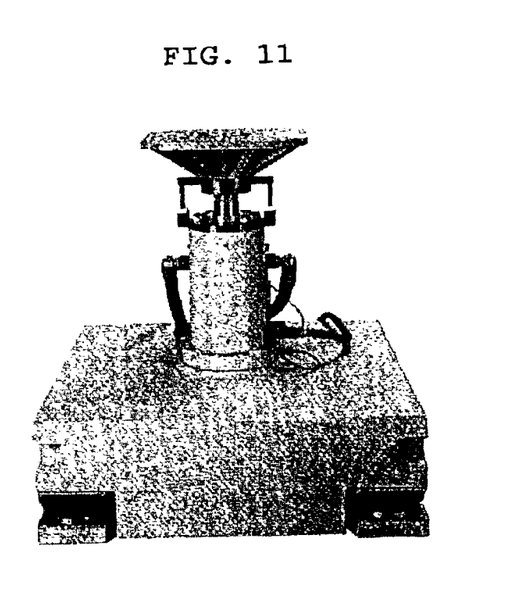
FIG. 11 shows a device for generating hydraulic vibration.
Figure 12:
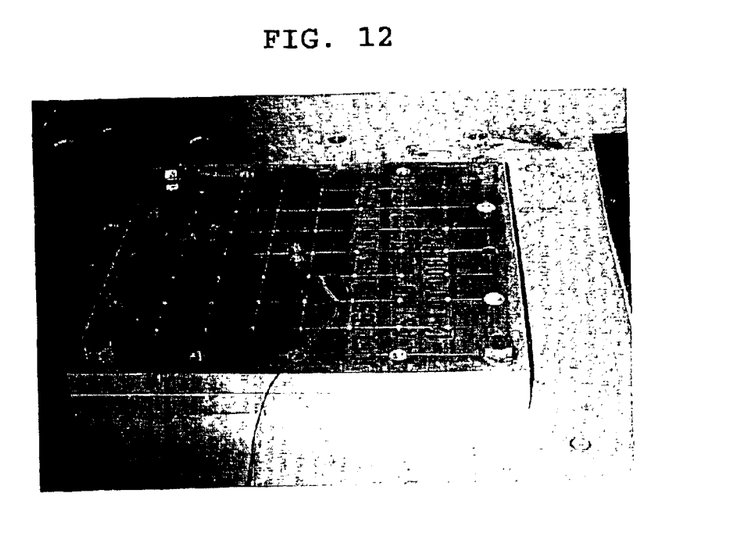
FIG. 12 is a photograph showing the fixturing table of the present invention actually mounted on a device for generating primary vibration.

Further, a device for generating unidirectional vibration used in the conventional reliability test (refer to FIGS. 9, 10 and 11) cannot generate multi-axes vibration waves of 6 degrees of freedom, and thus an auxiliary fixturing table which can easily generate vibration waves of 6 degrees of freedom for the HALT/HASS test has been required.

SUMMARY OF THE INVENTION

The object of the present invention is to provide a HALT/HASS fixturing table for generating secondary vibration using moving balls and multi-axes rails, wherein the table is constructed to generate multi-axes complex shock vibration waves of 6 degrees of freedom and mounted on a conventional vibration table for the HALT/HASS test, in order to adapt itself to an optimum vibration spectrum according to the changes of test specimens and various conditions and to enhance the maximum vibration level in the low frequency zone. The HALT/HASS test according to the present invention is conducted more effectively with smooth and flat vibration level in a high frequency zone.

Another object of the present invention is to provide a HALT/HASS fixturing table for generating secondary vibration using moving balls and multi-axes rails, wherein the table is installed on the conventional device for generating unidirectional vibration used in the conventional reliability test to generate secondary vibration, preferably random vibration waves in 6 degrees of freedom, so that the HALT/HASS test can be conducted more easily.

These and other objects of the present invention can be achieved by a HALT/HASS fixturing table for generating secondary vibration using moving balls and multi-axes rails comprising:

a lower panel placed on either a device for generating primary vibration or a fixturing table for use with the device for generating primary vibration, and having on the top surface thereof a plurality of horizontal rails and vertical rails formed in the shape of grooves of a certain depth;

moving balls inserted in the horizontal rails and the vertical rails of the lower panel to move in the horizontal and the vertical rails according to the vibration generated by the device for generating primary vibration;

a buffering member placed on the lower panel to absorb a part of the impact caused by movement of the moving balls and to diffuse the vibration; and a upper panel placed on the buffering member and fixed to the lower panel by joint means, a specimen for the HALT/HASS test being attached to the upper panel.

If vibration is generated by the device for generating primary vibration, the vibration is delivered to the lower panel, and the moving balls inserted in the horizontal and vertical rails of the lower panel move, thus generating secondary multiple impacts between the upper panel and the lower panel.

BRIEF DESCRIPTION OF THE DRAWINGS

The accompanying drawings, which are included to provide a further understanding of the invention and are incorporated in and constitute a part of this specification, serve to explain the principles of the invention together with the description, wherein:

FIG. 8 to FIG. 11 are photographs showing devices for generating primary vibration, wherein

DETAILED DESCRIPTION OF THE PREFERRED EMBODIMENTS

As shown in FIG. 1 to FIG. 4, the lower panel (4) of the fixturing table is formed in the shape of a board of a predetermined thickness, and it includes on the upper surface thereof a plurality of the horizontal rails (13) and the vertical rails (12) formed in multi-axes in the shape of grooves, into which the moving balls (3) are inserted.

Figure 1:
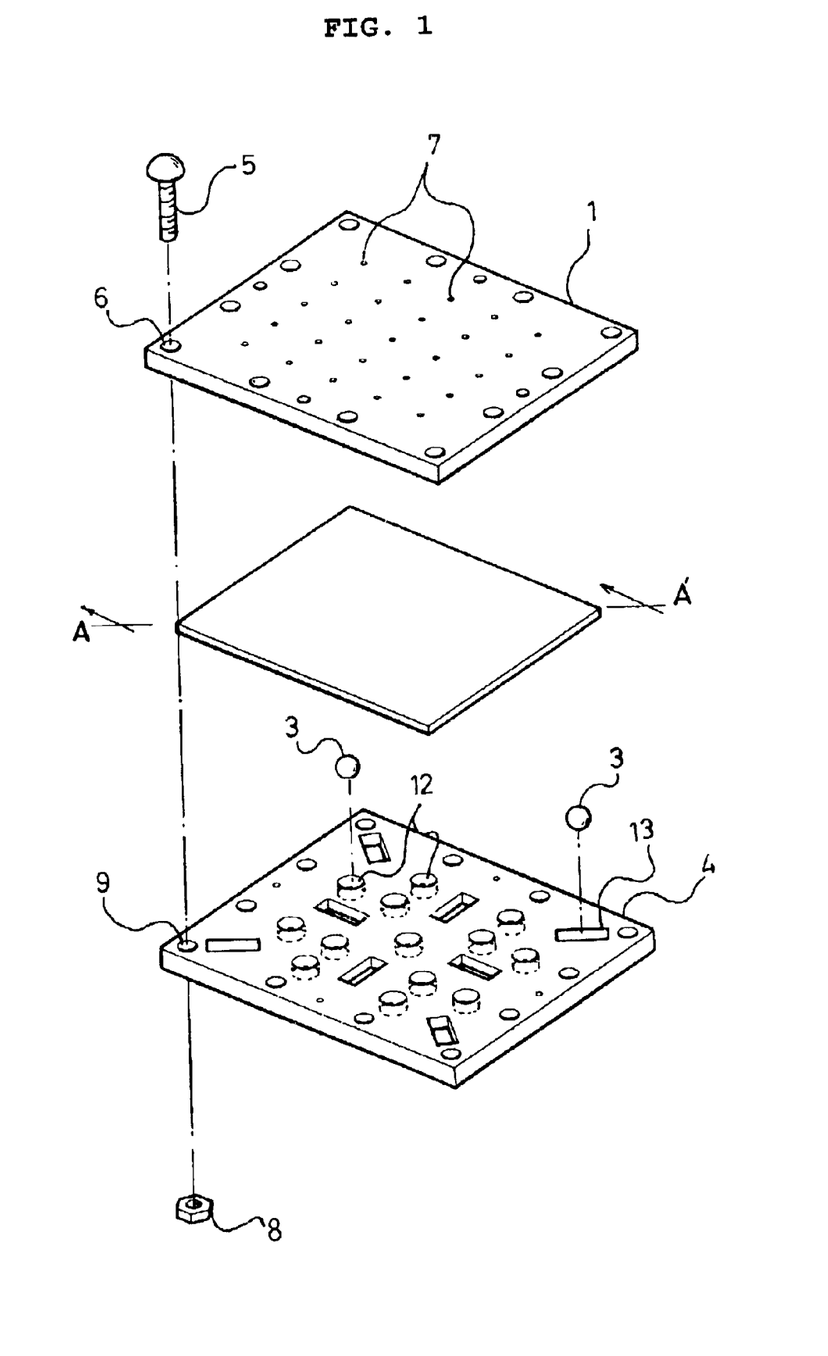
FIG. 1 is a disassembled perspective view of the fixturing table of the present invention which shows the upper panel (1), the lower panel (4) and the buffering member (2), and also shows the moving balls (3) inserted in the horizontal rails (13) and the vertical rails (12) formed in the lower panel (4)
Figure 3:
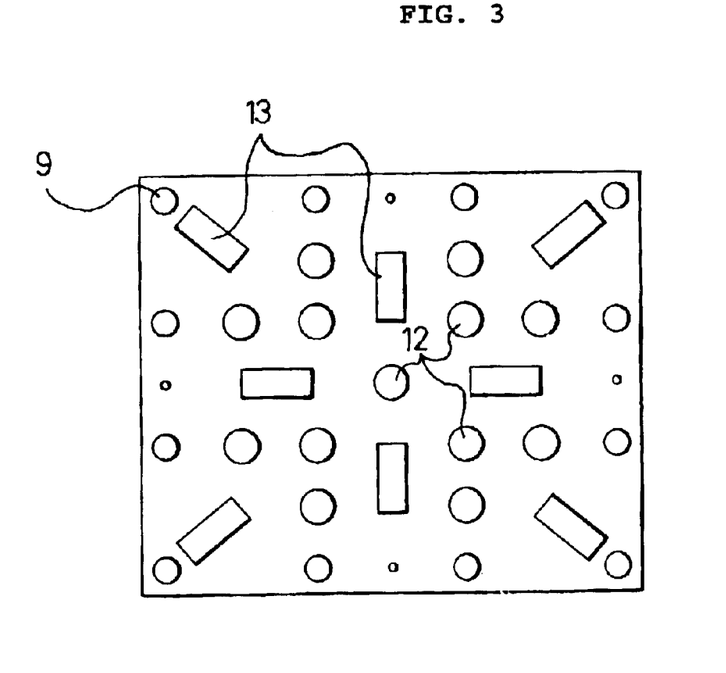
FIG. 3 is a plane view of the lower panel (4) of the fixturing table according to the present invention, which includes a plurality of horizontal rails (13) and vertical rails (12) formed in the shape of grooves of a certain depth, and second joint holes (9) with which the bolts (5) are fitted.

The respective horizontal rails (13) and vertical rails (12) are formed symmetrically with respect to the central point of the lower panel (4). The vertical rails (12) guide the moving balls (3) to move vertically, and the horizontal rails (13) of a predetermined length guide the moving balls (3) to move horizontally.

Further, the lower panel (4) includes the second joint holes (8) on its corners, through which the bolts (5) pass to connect the upper panel (1) to the lower panel (4).

Above the lower panel (4), the buffering member (2) of a predetermined size is mounted. The buffering member (2) is placed on the lower panel (4) after moving balls (3) are inserted into the horizontal and the vertical rails (13 and 12).

Figure 2:
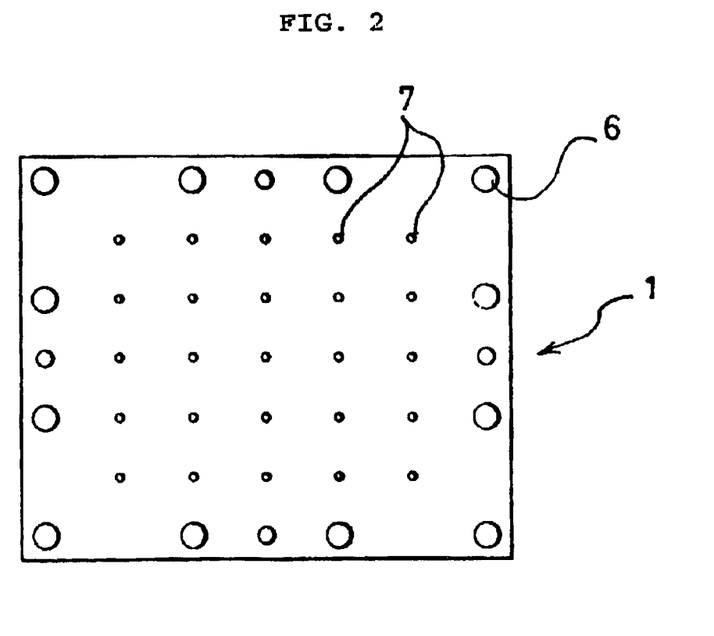
FIG. 2 is a plane view of the upper panel (1) of the fixturing table according to the present invention, which includes first joint holes (6) through which bolts (5) pass to fit with the lower panel (4), and holes (7) for the attachment of a test specimen thereto.

The upper panel (1) is provided on the top surface of the buffering member (2). The upper panel (1) is formed in the shape of a board having a predetermined thickness, and includes the first joint holes (6) in the corresponding locations to the second joint holes (8) of the lower panel (4) for the coupling with the lower panel (4) by the bolts (5) and the nuts (8). The upper panel (1) also includes holes (7) for the attachment of the test specimen for the HALT/HASS test thereto.

Figure 4:
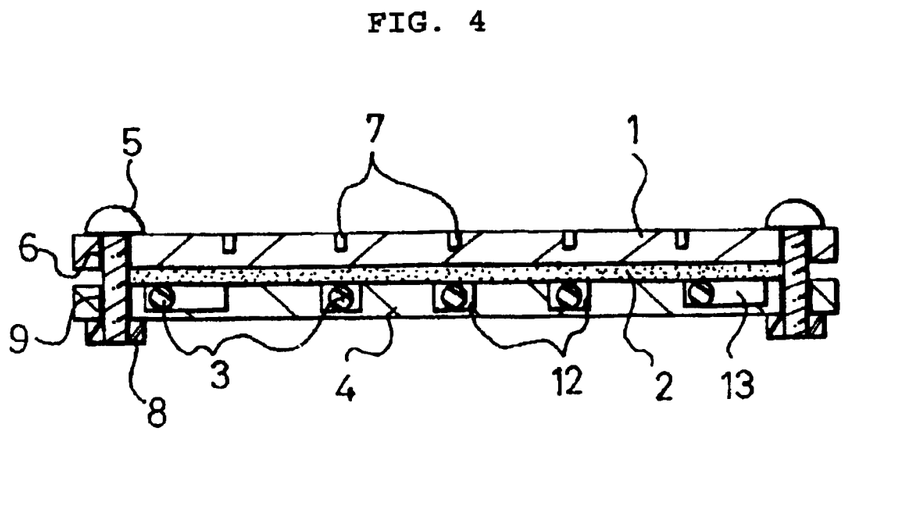
FIG. 4 is a sectional view of the fixturing table along the line A-A' of FIG. 1 in an assembled state, wherein the upper and lower panels (1 and 4) and the buffering member (2) are coupled by the bolts (5) and nuts (8)

The bolts (5) pass through the first joint holes (6) of the upper panel (1) and the second joint holes (9) of the lower panel (4), and one end of each of the bolts (5) extruded outside of the lower surface of the lower panel (4) is coupled with each of the nuts (8).

Figure 7:
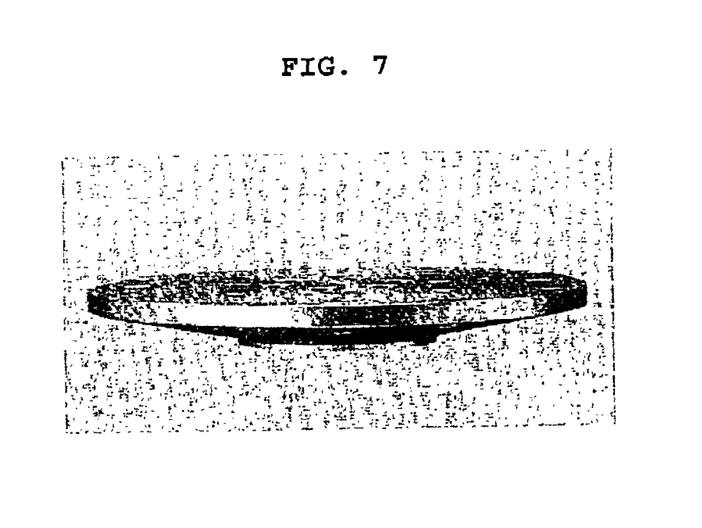
FIG. 7 is a photogragh showing a fixturing table used in conventional vibration tests.

The fixturing table of the present invention assembled as above is used by being placed on the conventional fixturing table as shown in FIG. 7 or the devices for generating primary vibration (20) as shown in FIG. 8 to FIG. 11.

The conventional fixturing table for use in general vibration tests as shown in FIG. 7 has been designed to have no resonance point in the range of test frequencies which are defined by test standard requirements, and unidirectional sine waves or unidirectional random waves have been used.

On the other hand, vibration waves used in the HALT/HASS tests which have recently been put to practical use are random vibration waves in multi-axes of 6 degrees of freedom, not unidirectional waves, so that resonance can be caused in a broad range of frequency zones.

Figure 5:
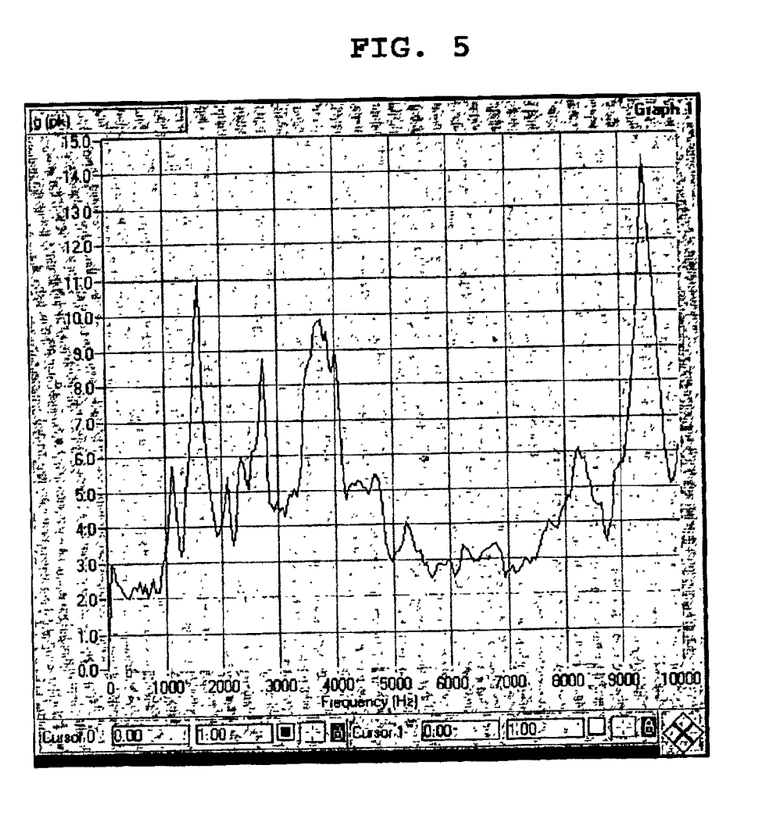
FIG. 5 is a graph showing an example of vibration spectrum without using the fixturing table according to the present invention, wherein the vibration spectrum of the conventional HALT/HASS pneumatic vibration mechanism is fixed and yields significantly high frequency energy and shows difficulties in elevating maximum vibration high in the low frequency zone for larger and more massive specimen.

However, the rigid vibration table for the HALT/HASS test using the conventional pneumatic cylinders as shown in FIG. 8 can generate multi-axes vibration of 6 degrees of freedom, but as shown in FIG. 5 the vibration spectrum was fixed and yielded significantly high frequency energy and it was difficult to enhance the maximum vibration in the low frequency zone.

In order to improve these difficulties, the fixturing table according to the present invention comprises the lower panel (4) including the multi-axes horizontal rails (13) and the multi-axes vertical rails (12) into which the moving balls (3) are inserted, the upper panel (1) to which the test specimen for the HALT/HASS test is attached, and the buffering member (2) placed between the upper panel (1) and the lower panel (4), to generate secondary multiple impacts on the upper panel (1) and the lower panel (4). Such constitution of the fixturing table of the present invention is to enhance the maximum vibration level in the low frequency zone and to create more various vibration spectrum zones.

Figure 6:
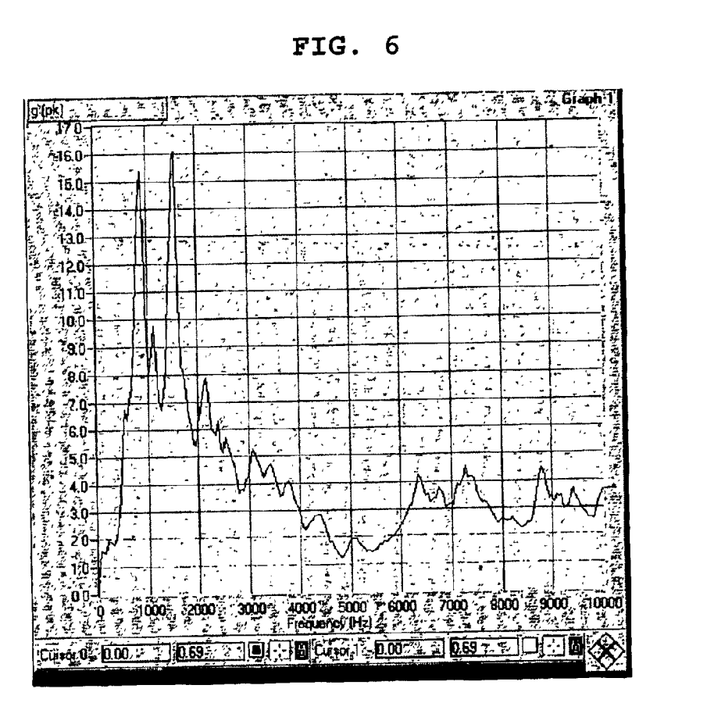
FIG. 6 is a graph showing an example of vibration spectrum using the fixturing table according to the present invention, wherein the vibration spectrum is variably converted and the maximum vibration in the low frequency zone is significantly increased, while the vibration level in the high frequency zone becomes smoother and flatter.

According to the fixturing table of the present invention, the vibration spectrum and the vibration level have been considerably changed in the low frequency zone of 300 Hz to 1,000 Hz and the high frequency zone of 9,000 Hz to 10,000 Hz as shown in FIG. 6.

Figure 13:
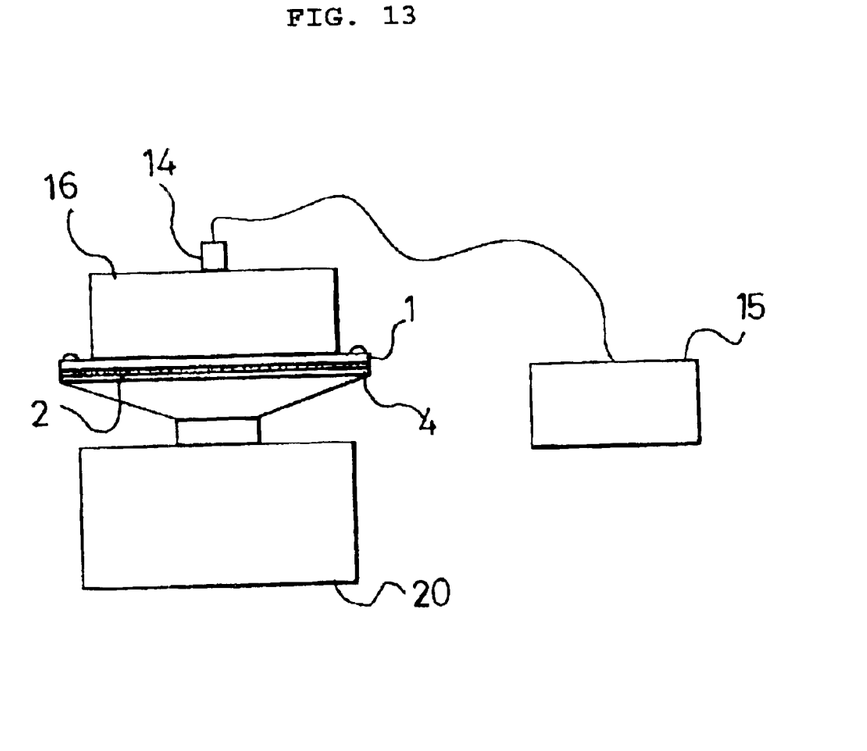
FIG. 13 is a schematic diagram showing the state of use of the fixturing table according to the present invention, wherein a test specimen (16) is attached to the upper panel (1) of the fixturing table of the present invention, and it includes a sensor (14) on its top to detect vibration characteristics of the test specimen and transmit the vibration characteristics to a frequency analyzer (15).

As shown in FIG. 13, the lower panel (4) is mounted on either the device for generating primary vibration (20) or on the fixturing table for use with the device for generating primary vibration (20), and the test specimen (16) is attached to the top surface of the upper panel (1).

The sensor (14) provided on the test specimen (16) is connected to the frequency analyzer (15) to make computers analyze the output results.

Accordingly, by the operation of the device for generating primary vibration (20), the moving balls (3) move along the horizontal and the vertical rails (13 and 12) formed in multi-axes in the lower panel (4), and cause secondary multiple impacts on the upper panel (1) and the lower panel (4) together with the buffering member (2).

According to the present invention described above, the HALT/HASS vibration spectrum can be varied and the vibration in 6 degrees of freedom can be generated with more stability.

Also, it becomes possible to effectively cause the acceleration and stimulate failure fast of the HALT/HASS test by forming various HALT/HASS vibration spectrum variable depending on objects of tests and test specimens by the changes and combinations of materials for the buffering member, sizes and numbers of moving balls and directions of the horizontal and the vertical rails.

That is, the fixturing table of the present invention improves the efficiency of the HALT/HASS test by adapting itself to various changes of the vibration spectrum appropriate for test specimens.

As mentioned above, according to the present invention, the vibration spectrum for the HALT/HASS test can be varied, and high maximum vibration in the low frequency zone and flatter and smoother vibration level in the high frequency zone can be achieved.

According to the present invention, the fixturing table shows prominent efficiency in the acceleration test for larger and more massive products which can be found more easily in the low frequency zone and in the acceleration test for inferior products which use electronic substrates such as small geometry components and soldering joints which can be found more easily in the flat and smooth high frequency zone.

Also, the fixturing table of the present invention can produce more stable vibration spectrum characteristics, so that it becomes possible to obtain the repeatability of the HALT test and shorten the time required for the HALT test with stimulating failure faster.

The fixturing table of the present invention shows excellent performance in the HASS test which requires more precise and variable vibration and frequency zone, by variably combining the factors such as the horizontal rails, the vertical rails, the moving balls and the buffering member.

In addition, the fixturing table according to the present invention can generate vibration in 6 degrees of freedom in addition to unidirectional vibration of the conventional vibration testers, thus enabling the HALT/HASS test to be conducted using the conventional device for generating unidirectional vibration, and enabling a new test field, i.e., the HALT/HASS test of complex waves (repetitive shock random waves in 6 degrees of freedom+sine waves) to be designed.

What is claimed is:

1. HALT/HASS fixturing table for generating secondary vibrations using moving balls and multi-axes rails comprising:

a lower panel placed on either a device for generating primary vibration or a fixturing table for use with the device for generating primary vibration, and having on a top surface thereof a plurality of horizontal rails and vertical rails;

a plurality of moving balls inserted in the horizontal rails and the vertical rails of the lower panel;

a buffering member placed on the lower panel to absorb a part of impact caused by movement of the moving balls and to diffuse the secondary vibrations; and a upper panel placed on the buffering member and fixed to the lower panel by fasteners, a specimen for a HALT/HASS test being attached to the upper panel;

wherein the horizontal and the vertical rails are formed in rectangular groove shape and cylindrical groove shape respectively so that the moving balls inserted in the horizontal and the vertical rails move vertically in the vertical grooves and horizontally in the horizontal grooves to generate the secondary vibrations in response to generation of the primary vibration;

wherein size, weight, and quantity of the moving balls are variable according to the specimen attached to the upper panel for the HALT/HASS test; and wherein direction, quantity, width and length of the horizontal and the vertical rails are variable according to the specimen attached to the upper panel for the HALT/HASS test.

2. The HALT/HASS fixturing table according to claim 1, wherein the moving balls freely movable in either direction within the horizontal and the vertical rails.

3. The HALT/HASS fixturing table according to claim 1, wherein the horizontal and the vertical rails are perpendicular to one another.

4. The HALT/HASS fixturing table according to claim 1, wherein the horizontal and the vertical rails extend in at least two axes.

* * * * *